United States Patent [19]

Steer

[11] Patent Number: 4,695,279
[45] Date of Patent: Sep. 22, 1987

[54] INCONTINENCE BRIEFS AND PANTS

[75] Inventor: Graham E. Steer, Surrey, England

[73] Assignee: Craig Medical Products Limited, East Grinstead, England

[21] Appl. No.: 853,533

[22] Filed: Apr. 18, 1986

[30] Foreign Application Priority Data

Apr. 29, 1985 [GB] United Kingdom ............... 8510876
Jul. 16, 1985 [GB] United Kingdom ............... 8517871
Aug. 22, 1985 [GB] United Kingdom ............... 8521020

[51] Int. Cl.$^4$ ............................................. A61F 13/16
[52] U.S. Cl. ...................................... 604/397; 2/406; 604/401
[58] Field of Search ................... 2/408, 406, 403, 400, 2/409, 405; 128/529, 526, 527, 528; 604/385 R, 385 A, 397, 398, 401

[56] References Cited

U.S. PATENT DOCUMENTS

| 2,319,138 | 5/1943 | Kneibler | 2/405 X |
| 2,369,773 | 2/1945 | Brenner | 2/405 X |
| 2,381,232 | 8/1945 | Stone | 128/529 X |
| 2,476,585 | 7/1949 | Cohen | 2/408 X |
| 2,522,009 | 9/1950 | Wohlman | 128/529 |
| 3,224,448 | 12/1965 | Diebold | 2/408 X |
| 4,301,550 | 11/1981 | Carver | 2/408 |

Primary Examiner—H. Hampton Hunter
Attorney, Agent, or Firm—Lawrence S. Levinson; Sanford J. Asman

[57] ABSTRACT

A pair of incontinence pants or briefs includes a pocket located in the crotch region and defined by an outer wall of a liquid-impermeable material which is longer than it is wide and an inner wall of like material whose edges define a substantially oval hole. A portion of the inner wall overlaps, but it not connected to another thereof and the edges are crossed over one another at one end of the pocket.

6 Claims, 4 Drawing Figures

INCONTINENCE BRIEFS AND PANTS

BACKGROUND OF THE INVENTION

This invention relates to incontinence briefs and pants suitable for wearing by males and females.

Prior proposals for incontinence briefs or pants which were suitable to be worn by females and which were provided with means for attaching or accommodating pads to absorb urine or menstrual discharge are to be found in numerous prior patent specifications. In particular, such devices are described in British patent specification Nos. 292,464; 358,765; 436,869; 855,020; 878,455 and 888,827.

In British Pat. No. 1 143 419 it was proposed that a so-called sanitary slip should have a flexible support for containing or locating an absorbent member. The slip and support have and are connected together by corresponding fastening elements. British Pat. No. 1 178 212 discloses a sanitary garment comprising a stretchable panty body having in its crotch section a lining of waterproof material, the ends of which are respectively attached to the front and back panels of the panty form, whereas its side edges are gathered to the respective adjoining leg openings, the lining at each end being further covered with sections of waterproof material forming a front and a back pocket for inserting the ends of an absorbent pad, such as a sanitary napkin. In such a garment there is folded a double layer of thin waterproof material weldable to the lining and welded thereto through a pair of spaced welding seams forming a gap for maintaining the end of the absorbent pad.

It has been suggested in International Patent Application Publication No. WO85/03430 (BRIER) that a disposable waterproof encasement for an absorbent sanitary pad should be releasably fixed to an undergarment to convert that garment into a sanitary panty or a stress incontinence garment. A similar idea has been previously proposed in British Pat. No. 1 441 087 (KANGA), which provides a pocket for a removable pad of absorbent material which absorbs accidentally-discharged urine when in use.

British Pat. No. 1 580 550 (Fail Safe Apparel Corporation; invention PAPAJOHN) relates to a panty with a holder for a sanitary napkin. The holder is of waterproof material and opens with VELCRO flaps at either end so that the sanitary napkin can be inserted or removed. In normal wear, the flaps are fixed closed to retain the napkin in place. It is a feature of this arrangement, which is not particularly disadvantageous in the context of a holder for a sanitary napkin, that the holder is open-ended, in the sense that the folding over of the flaps into the closed position, i.e., so they are adjacent the outer wall of the holder, provides no liquid barrier.

SUMMARY OF THE INVENTION

For incontinence briefs or incontinence pants intended for normal or daily wear, rather than hospital or geriatric use, it is desirable to have a pocket which (i) allows easy insertion and removal of an absorbent pad, (ii) securely retains a pad in position once inserted, (iii) is comfortable and yields to a certain extent in response to movement by the wearer, (iv) does not bulge and is unobtrusive, (v) is easily fixed in the garment either during its manufacture or thereafter, and (vi) prevents or reduces the likelihood of any urine reaching fabric parts of the garment. The present invention has been developed in an attempt to address these conflicting and demanding requirements.

According to one aspect of the invention, a pair of incontinence pants or briefs includes a pocket located in the crotch region and defined by an outer wall of a liquid-impermeable material which is longer than it is wide and an inner wall of like material whose edges define a substantially oval hole, a portion fo the inner wall overlapping but not connected to another portion thereof and the edges being crossed over one another at one end of the pocket. As used herein, the words "inner" and "outer" are used in relation to a garment as worn.

According to a second aspect of the invention, a pair of incontinence briefs or pants includes a pocket located interiorly of the fabric of the crotch region, said pocket having an inner wall and an outer wall both of liquid impermeable material such as thin rubber or rubberized cloth, the pocket being open at a region facing towards the vagina or male genitalia when the briefs or pants are being worn by a wearer, the edges of the opening being partly or wholly elasticated.

An advantage of the arrangement disclosed herein is that it allows easy insertion of an absorbent pad and yet securely retains the absorbent pad in its effective position during normal wear, including during sporting activities.

Preferably, the outer longitudinal edges of the inner wall portions and the outer wall are not stitched to the material of the garment but are stitched together by respective seams. This results in a free-floating fixing of the middle portion of the waterproof pocket which is inwardly spaced from the crotch portion of the garment. This feature has the advantages firstly that the same manufacturing equipment can be used to make pants which include a pocket, as well as those which do not; and secondly, that the free floating arrangement results in a less stiff and more comfortable crotch portion and which permits minor adjustments of the location of the waterproof pocket by the wearer.

With such an arrangement, the outer and inner walls are positioned so as to retain, in use, the elongated absorbent pad in the pocket with its marginal edges sandwiched between the inner and outer walls and its central region in registry with the hole ready to absorb any urine which may be discharged. The elasticated edges assist in preventing dislodgement of the absorbent pad. The arrangement does not require the awkward end insertion procedure, such as exemplified in British Pat. No. 1 441 087.

In the arrangement according to the invention particularly disclosed herein, the seams around all four sides of the substantially rectangular pocket prevent liquid exiting in any of these areas, in contrast to the arrangement in Pat. No. 1 580 550 referred to above.

DETAILED DESCRIPTION OF THE PREFERRED EMBODIMENT

The present invention aims to provide versatile briefs and pants especially suitable for wear by active persons who suffer mild incontinence. As will be understood, for user acceptability, it is desirable that the pants and briefs should approximate as closely as possible currently available styles and fashions intended for those not incontinent. The present invention aims to meet this need.

Figure 1:
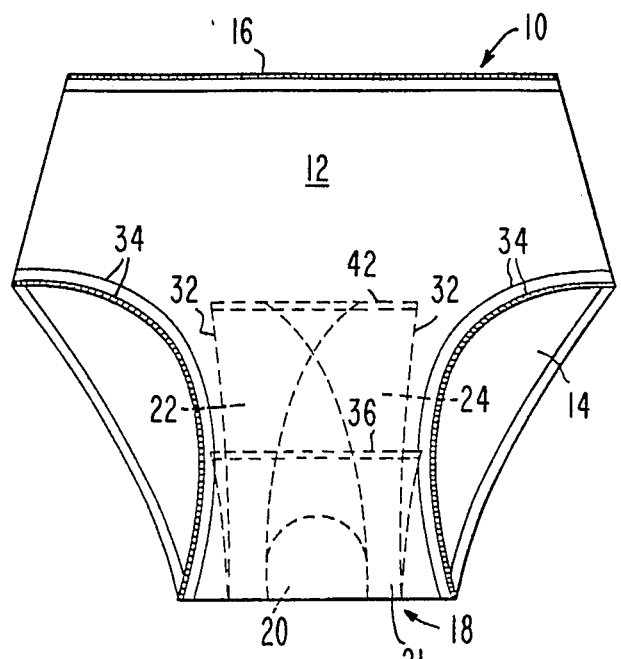
FIG. 1 is a front view of a pair of incontinence pants suitable for wearing by a female and in accordance with one example of the invention.
Figure 2:
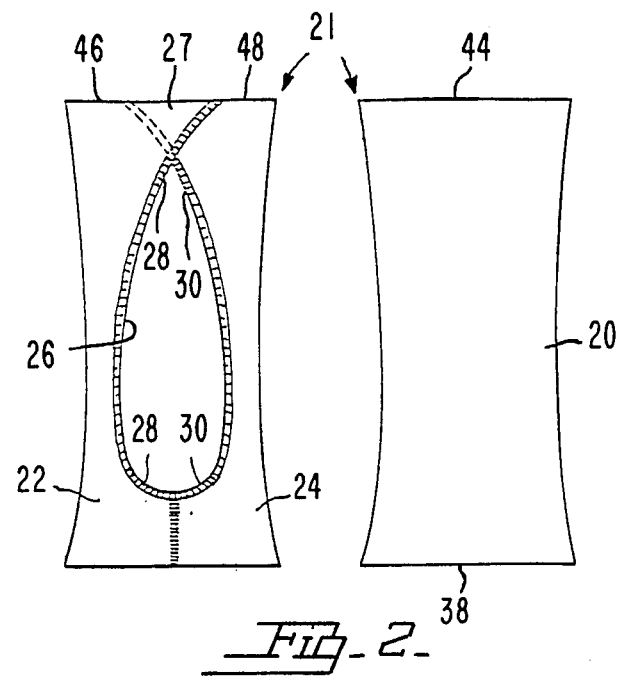
FIG. 2 is a an illustration showing the shape of two liquid impermeable panels which may be used to define a pocket for receiving an absorbent pad in the incontinence pants of FIG. 1.

Referring now to FIGS. 1 and 2, the illustrated incontinence pants (also called briefs) 10 for female were have front and rear panels 12, 14 of conventional elasticated fabric, a waist band 16, and a crotch portion 18. The crotch portion 18 has a pocket 21 located interiorly thereof defined by an outer wall 20 and inner walls 22, 24 of liquid impermeable material which may be a liquid impermeable sheet of a plastic or of a fabric. The outer wall 20 is located within, but closely adjacent and parallel to, the fabric of the crotch portion 18 of the briefs 10. The inner walls 22, 24 define an opening 26, as shown in FIG. 2, therein which serves as the path for any expelled urine to reach an absorbent pad (not shown for clarity of illustration). The pad is inserted in and is located in the pocket 21 formed between the outer wall 20 and the inner walls 22, 24. The opening 26 has its boundary defined by the edges 28, 30 of the respective walls 22, 24 and these edges are preferably elasticated. They may be provided with a suitable binding, as illustrated in FIG. 2. The opening 26 is illustrated as substantially oval but may be of any convenient shape. A substantially oval hole is preferred.

In order to manufacture the briefs 10, the outer wall or panel 20 is secured to the inner walls or panels 22, 24 and the resulting pouch or pocket 21 is held in place in the briefs 10 by cross seams 36, 42. The cross-seam 36, shown in FIG. 1, connects the rear panel 14 to the ends 38, 40 of the walls 20, 22, 24. At the front of the briefs 10, a cross seam 42 connects an edge 44 of the outer wall or panel 20, shown in FIG. 2, to the front fabric panel 12 of the briefs 10. The corresponding ends 46, 48 of the respective inner walls 22, 24 are seamed to the front panel 12 by the same cross seam 42. The inner walls 22, 24 overlap at the region 27, shown in FIG. 2. They are sewn together along their respective bottom edges, but they are not sewn together at their along their inner edges 28, 30 in this region 27 in order to provide a gap between the panels 22, 24. This gap in the region 27 is an important feature of the present invention and is at the top front end of the pocket 21, as shown in FIG. 1. It serves to facilitate insertion and removal of the absorbent pad (not shown).

Figure 4:
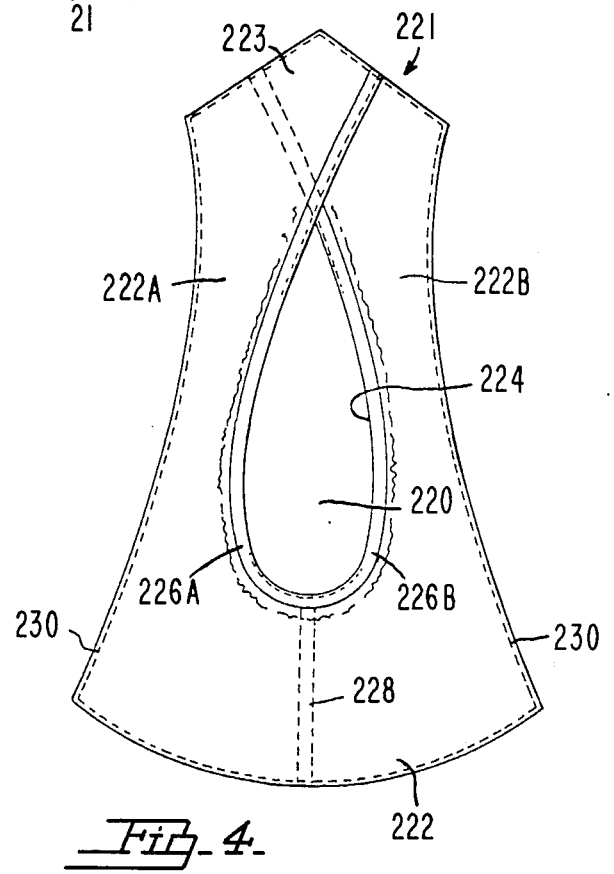
FIG. 4 is an exploded view illustrating the construction of the pocket for insertion into the Y-front type briefs in accordance with FIG. 3.
Figure 3:
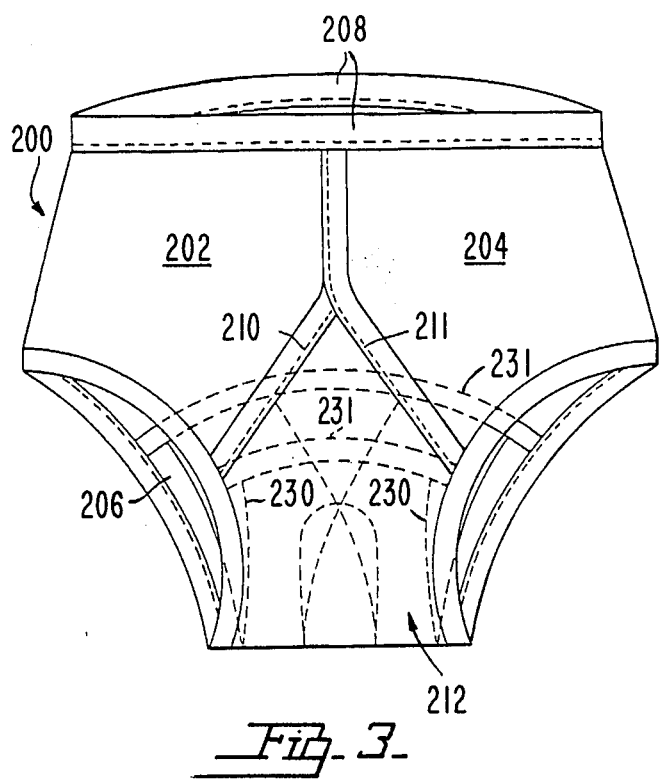
FIG. 3 is a front view of a pair of Y-front type briefs suitable for wearing by males and in accordance with a second example of the invention.

An alternative embodiment of the invention 200 is illustrated in FIG. 3 which shows male briefs 200 of the Y-front type. The illustrated briefs 200 have conventional front fabric panels 202, 204 which are a continuation of a conventional rear panel 206. The fabric of the briefs 200 may be a conventional elasticated fabric. The briefs 200 have a conventional waistband 208. A "Y" seam 210, 211 joins the panels 202, 204 to a crotch portion 212. In this embodiment of the invention 200 the crotch portion 212 has a pocket 221 fixed, e.g. by stitching to the inner surface thereof, to the briefs 200. The pocket, which is illustrated in FIG. 4, consists of an outer wall 220 of waterproof material and an inner wall 222. The inner wall 222 is made up of two wall portions 222A, 222B which have edges 226A, 226B, respectively, which define a substantially oval-shaped opening 224 in the inner wall 222. The edges 226A, 226B of the opening 224 are preferably ruched and bound with elastic material. The two inner wall portions 222A, 222B are seamed together at 228 at the end of the pocket 221 which is at the rear when the garment 200 is worn, and each wall portion 222A, 222B is seamed as shown at 230 to the outer wall 220 around the periphery of the wall 220, thereby defining the pocket 221 whose entrance for urine is the opening 224 previously referred to. Any urine which may have been released or leaked by the wearer, when the garment 200 is worn, reaches the absorbent pad via the opening 224. As shown in FIG. 4, the upper portion 223 of the pocket 221 is pointed in order to correspond with the structure of the conventional Y-front briefs 200. Of course, the upper region 223 of the pocket 221 could instead be of a different shape if desired, e.g. "square ended" similar to the arrangement for female pants shown in FIGS. 1 and 2.

The crotch portion 212 of the briefs 200, shown in FIG. 3, is joined by the seam 211 to the fabric panel 204. In line with conventional Y-front construction, a gap is left between the seam 210, which attaches the pocket 221 to the crotch portion 212, and the seam (not shown, but located immediately behind seam 210 of FIG. 3) which defines the front upper edge of the panel 202. This gap permits the wearer, should he so desire, to insert an absorbent pad into the pocket from outside the garment by passing it through this gap. As an alternative however, he may insert the absorbent pad by removing or partly removing the briefs 200 from his body, pulling apart the edges 226A, 226B, and inserting the pad in that way from the interior of the garment 200. This facility whereby an absorbent pad may be inserted by either procedure is believed to be a unique and valuable feature in male incontinence garments.

The waterproof pocket 221 constructed in the manner described is preferably stitched by seams 231 at the ends of the pocket 221, as shown in FIG. 3, to the fabric panel 212, thereby forming the crotch portion 212. With the illustrated construction, the comfort and appearance of conventional Y-front briefs are obtained in incontinence briefs.

It will be seen that there have been particularly described and illustrated herein briefs or pants which can accommodate an absorbent pad, which are comfortable to wear, which are of a modern fashionable design, and in which the pad can readily be removed and replaced with the minimum of awkward manipulation by the wearer. The designs are such that manufacture requires no special equipment and is relatively inexpensive.

It will be understood that obvious modifications and variations, e.g., in material chosen, pattern and dimensions will occur to one skilled in the art, and the invention is intended to include all such modifications and variations.

I claim:

1. A pair of incontinence pants or briefs including a pocket located in the crotch region, the pocket defined by an outer wall of a liquid-impermeable material which is longer than it is wide and an inner wall of like material, the inner wall constructed of two pieces whose edges define a substantially oval hole, a portion of the one piece of the inner wall overlapping but not connected to a portion of the second piece of the inner wall, their edges being crossed over one another at one end of the pocket.

2. The incontinence of briefs or pants of claim 1 in which said inner and outer walls are connected together by side seams and end seams, and said end seams, but not said side seams, connect said pocket to said briefs or pants.

3. The incontinence briefs or pants of claim 1 in which the free edges of the inner wall are elasticated.

4. The incontinence briefs or pants of claim 3 in which said inner and outer walls are connected together by side seams and end seams, and said end seams, but not said side seams, connect said pocket to said briefs or pants.

5. A pair of incontinence briefs or pants including a pocket located interiorly of the fabric of the crotch region, said pocket having an inner wall and an outer wall both of liquid impermeable material, the pocket having an opening which extends through its inner wall towards the body of the wearer when said briefs or pants are being worn, the edges of said opening being partly or wholly elasticated.

6. The incontinence briefs or pants of claim 5 in which said inner and outer walls are connected together by side seams and end seams, and said end seams, but not said side seams, connect said pocket to said briefs or pants.

* * * * *